United States Patent [19]
Petersen

[11] Patent Number: 5,331,473
[45] Date of Patent: Jul. 19, 1994

[54] CONTROLLED REFLECTION VIEWING SYSTEM

[76] Inventor: T. Douglas Petersen, 17831 Lassen St., #307, Northridge, Calif. 91325

[21] Appl. No.: 92,906

[22] Filed: Jul. 19, 1993

[51] Int. Cl.⁵ .............................................. G02B 5/00
[52] U.S. Cl. .................................. 359/894; 359/815; 359/613; 2/5; 2/8; 2/426
[58] Field of Search ............... 359/894, 815, 819, 793, 359/794, 795, 601, 602, 610, 613; 2/5, 6, 7, 8, 9, 205, 421, 426, 427, 428

[56] References Cited
U.S. PATENT DOCUMENTS

| | | |
|---|---|---|
| 3,444,561 | 5/1969 | Boyer ............................................ 2/8 |
| 3,577,563 | 5/1971 | Raschke ........................................ 2/8 |
| 3,944,345 | 3/1976 | Decorato ..................................... 359/815 |
| 4,397,045 | 8/1983 | Schonwetter et al. ...................... 2/5 |
| 4,916,753 | 4/1990 | Khaedung .................................... 2/8 |
| 5,029,342 | 7/1991 | Stein et al. ................................... 2/8 |
| 5,220,453 | 6/1993 | McKinley et al. ......................... 359/613 |

Primary Examiner—Loha Ben
Attorney, Agent, or Firm—Robert M. Sperry

[57] ABSTRACT

An improved double-lensed viewing system having a first lens or shield formed of shatterproof glass or plastic and mounted at an angle of at least 05° from the vertical, together with a second lens or shield formed of partially opaque material mounted in optical alignment with the first lens or shield and extending parallel to the vertical.

9 Claims, 1 Drawing Sheet

CONTROLLED REFLECTION VIEWING SYSTEM

BACKGROUND

1. Field of Invention

This invention relates to viewing systems and is particularly directed to improved viewing systems for welding helmets, goggles and the like which eliminate reflections, multiple images and the like.

2. Prior Art

It is well known in the welding art that some means must be provided to protect the welder's eyes against the brilliance of the welding arc and against sparks and other debris which may be thrown off during the welding operation and which can cause damage or blindness. Many types of qoggles and helmets have been proposed heretofore for providing such protection. However, many of the prior art qoggles and helmets have employed double-lensed devices having a first lens or shield formed of shatterproof glass or plastic and a second lens or shield formed of partially opaque material to reduce the intensity of light incident on the weldere's eyes. Unfortunately, light passing through such double-lensed devices often produces reflections or multiple images which are sometimes difficult to distinguish from the real object and which are always distracting and confusing to the welder. Thus, none of the prior art double-lensed viewing systems have been entirely satisfactory.

BRIEF SUMMARY AND OBJECTS OF INVENTION

These disadvantages of prior art viewing systems are overcome with the present invention and improved viewing systems are provided which completely eliminate undesired reflections and false images without impairing the view of the actual object.

The advantages of the present invention are preferably attained by providing a double-lensed viewing system having a first lens or shield formed of shatterproof glass or plastic and mounted at an angle of at least 05° from the vertical, together with a second lens or shield formed of partially opaque material mounted in optical alignment with the first lens or shield and extending parallel to the vertical.

Accordingly, it is an object of the present invention to provide an improved viewing system.

Another object of the present invention is to provide an improved double-lensed viewing system.

An additional object of the present invention is to provide an improved viewing system which eliminates reflections and false images.

A further object of the present invention is to provide an improved double-lensed viewing system which eliminates reflections and false images.

A specific object of the present invention is to provide an improved double-lensed viewing system having a first lens or shield formed of shatterproof glass or plastic and mounted at an angle of at least 05° from the vertical, together with a second lens or shield formed of partially opaque material mounted in optical alignment with the first lens or shield and extending parallel to the vertical.

These and other objects and features of the present invention will be apparent from the following detailed description, taken with reference to the figures of the accompanying drawing.

DETAILED DESCRIPTION OF THE INVENTION

Figure 1:
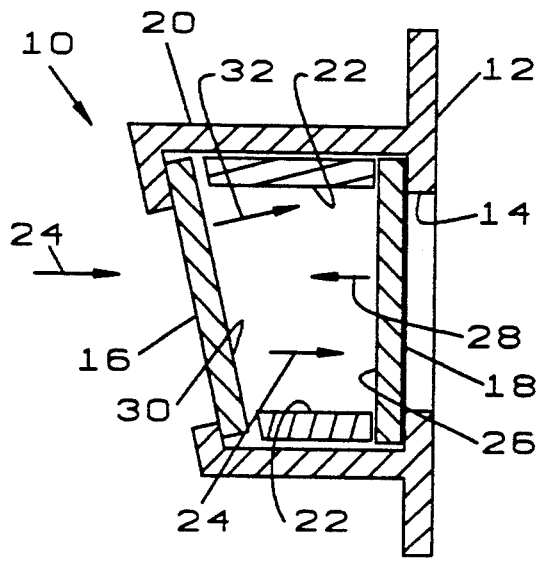
FIG. 1 is a vertical section through a viewing system embodying the present invention.

In that form of the present invention chosen for purposes of illustration in FIG. 1, a double-lensed viewing system is shown, indicated generally at 10, mounted in a suitable support 12, such as a welding helmet, goggles frame or the like. formed with an opening 14 for viewing. As seen in FIG. 1, the viewing system 10 comprises a pair of lenses 16 and 18 mounted in optical alignment with each other within a frame 20. The lenses 16 and 18 are spaced apart and the first lens 16 is mounted at an angle of at least 05° with the vertical, while the second lens 18 is mounted parallel to the vertical. Preferably, one of the lenses, for example lens 16, will be formed of clear shatterproof material, while the other, for example lens 18, will be darkened, to protect the weldere's eyes against the brilliance of the welding arc. If desired, suitable cushioning means 22, such as rubber blocks, may be located between the lenses 16 and 18 to maintain the lenses 16 and 18 in their respective positions within the frame 20, to cushion the lenses 16 and 18 against damage to vibration or the like and to maintain the desired angular relationship between the lenses 16 and 18.

In use, the welder puts on the helmet or goggles 12 and looks through the viewing opening 14 to observe the welding operation. Because the first lens 16 is mounted at an angle of at least 05° with respect to the second lens 18, light, indicated by arrows 24, passing through the first lens 16 and reflecting off the front surface 26 of the second lens 18, as indicated by arrow 28, will be reflected at an angle by the rear surface 30 of lens 16, as indicated by arrow 32, and will prevent the welder from seeing the reflection. Thus, double images are averted and the welder sees only the true situation.

Figure 2:
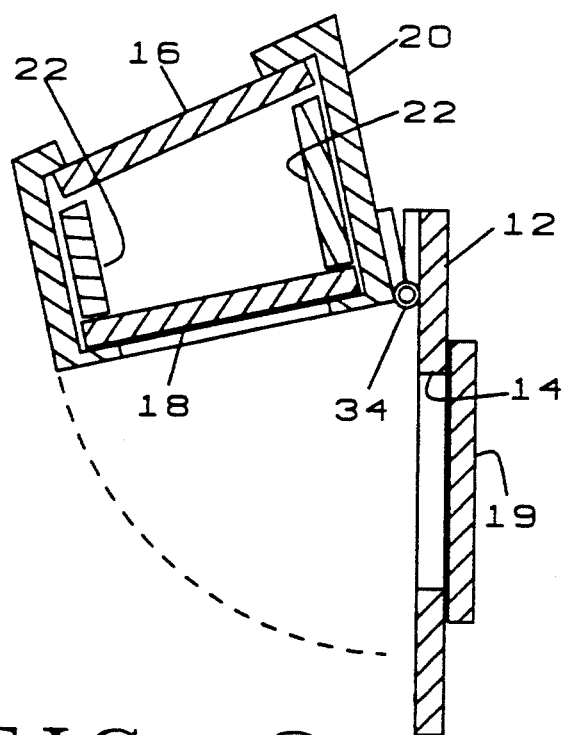
FIG. 2 is a view, similar to that of FIG. 1, showing an alternative form of the viewing system of FIG. 1.

FIG. 2 shows an alternative form of the viewing system of FIG. 1 wherein the frame 20 is hingedly mounted on the support member 12, as by hinge 34. Preferably, a transparent plate 19 will be mounted to also cover the window 14 to prevent chips or other debris from flying through the opening 14 to possibly injure the usere's eye, while the frame 20 is in the raised position. With this arrangement, the welder can raise the frame 20, to the position seen in FIG. 2, to facilitate viewing prior to igniting the welding torch to facilitate setting up the welding operation. Subsequently, the welder can swing the frame 20 downward about hinge 34, to the position seen in FIG. 1, whereupon the lenses 16 and 18 will serve to protect the welder's eyes during the welding operation.

Figure 3:
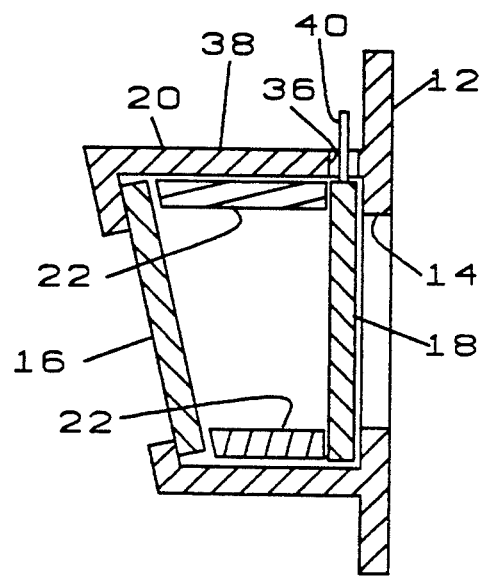
FIG. 3 is a view, similar to that of FIG. 1, showing another alternative form of the viewing system of FIG. 1.

FIG. 3 shows another alternative form of the viewing system of FIG. 1. In this version, the frame 20 has a slot 36 formed in the upper portion 38 thereof and the second lens 18 is provided with a tab 40, which enables the welder to slide the second lens 18 upward and downward through the slot 36. Thus, the welder can grasp the tab 40 and raise the second lens 18 to permit the welder to have an unobstructed view of the welding operation and, subsequently, can lower the second lens 18 to protect the welder's eyes against the brilliance of the welding arc.

Obviously, numerous other variations and modifications can be made without departing from the spirit of the present invention. Therefore, it should be clearly understood that the forms of the present invention described above and shown in the figures of the accompanying drawing are illustrative only and are not intended to limit the scope of the present invention.

What is claimed is:

1. A viewing system comprising:
   a support member,
   a frame mounted on said support member,
   a pair of lenses mounted within said frame in optical alignment with each other and with one of said lenses mounted at an angle of at least 05° with respect to the other.

2. The viewing system of claim 1 wherein:
   said support member is a welding helmet.

3. The viewing system of claim 1 wherein: said support member is the frame of a pair of goggles.

4. The viewing system of claim 1 wherein:
   said frame has a forward end and a rear end, and
   the first of said lenses is mounted adjacent the forward end of said frame while the second of said lenses is mounted adjacent the rear end of said frame.

5. The viewing system of claim 1 wherein:
   one of said lenses is mounted parallel to the vertical, while the other of said lenses is mounted at an angle of at least 05° to the vertical.

6. The viewing system of claim 5 wherein:
   said frame has a forward end and a rear end, and
   said one of said lenses is mounted adjacent said forward end of said frame while said other of said lenses is mounted adjacent said rear end of said frame.

7. The viewing system of claim 1 wherein:
   said frame is hingedly secured to said support member.

8. The viewing system of claim 1 further wherein
   said frame has an upper surface with a slot formed therein, and
   one of said lenses has a tab secured thereto extending through said slot to facilitate raising and lowering said one of said lenses through said slot.

9. The viewing system of claim 1 further comprising:
   cushioning means located between said lenses and serving to protect said lenses against damage due to vibration.

* * * * *